United States Patent [19]
Earp, III et al.

[11] Patent Number: 5,585,269
[45] Date of Patent: Dec. 17, 1996

[54] ISOLATED DNA ENCODING C-MER PROTOONCOGENE

[75] Inventors: H. Shelton Earp, III; Doug Graham; Thomas L. Dawson, all of Chapel Hill, N.C.; David L. Mullaney, Middletown, Conn.; Hiram R. Snodgrass, Powell, Ohio

[73] Assignee: The University of North Carolina at Chapel Hill, Chapel Hill, N.C.

[21] Appl. No.: 252,626

[22] Filed: Jun. 2, 1994

[51] Int. Cl.$^6$ ............ C07K 14/705; C07K 19/00; C12N 15/12; C12N 15/62
[52] U.S. Cl. ............ 435/252.3; 435/69.1; 435/69.7; 435/320.1; 530/350; 536/23.4; 536/23.5
[58] Field of Search ............ 435/69.1, 69.7, 435/252.3, 320.1; 530/350; 536/23.4, 23.5

[56] References Cited

FOREIGN PATENT DOCUMENTS

| | | |
|---|---|---|
| WO93/00425 | 1/1993 | WIPO . |
| WO93/14124 | 7/1993 | WIPO . |
| WO94/10197 | 5/1994 | WIPO . |

OTHER PUBLICATIONS

H. Earp, et al; Characterization of Distinct Tyrosine–specific Protein Kinases in B and T Lymphocytes, *J. Biol. Chem.* 260:4351–4356 (1985).

H. Earp, et al; Membranes from T and B Lymphocytes Have Different Patterns of Tyrosine Phosphorylation, *Proc. Natl. Acad. Sci. USA* 81:2347–2351 (1984).

J. O'Bryan et al; axl A Transforming Gene Isolated from Primary Human Myeloid Leukemia Cells, Encodes a Novel Receptor Tyrosine Kinase, *Mol. Cell Biol.* 11:5016–5031. (1991).

C. Lai & G. Lemke, An Extended Family of Protein–Tyrosine Kinase Genes Differentially Expressed in the Vertebrate Nervous System, *Neuron* 6:691–704 (1991).

D. K. Graham et al; Cloning and mRNA Expression Analysis of a Novel Human Protooncogene, c-mer, *Cell Growth & Differentiation* 5:647–657 (1994).

*Primary Examiner*—Stephen G. Walsh
*Assistant Examiner*—John D. Ulm
*Attorney, Agent, or Firm*—Bell, Seltzer, Park & Gibson

[57] ABSTRACT

Isolated DNAs encoding a mammalian c-mer receptor which exhibits c-mer protooncogene activity and tyrosine kinase activity are disclosed. Also disclosed are vectors containing such DNAs, host cells containing such DNAs, c-mer receptor proteins, and soluble axl receptors, chimeric proteins including the extracellular domain of the c-mer receptor and DNAs encoding such chimeric proteins, and antibodies which specifically bind the c-mer receptor.

22 Claims, 1 Drawing Sheet

ISOLATED DNA ENCODING C-MER PROTOONCOGENE

This Invention was made with Government support under grant number DK31683 from the National Institutes of Health. The Government has certain rights to this invention.

FIELD OF THE INVENTION

The present invention relates to protooncogenes in general, and particularly relates to an protooncogene which codes for a receptor having tyrosine kinase activity in the axl oncogene family.

BACKGROUND OF THE INVENTION

Tyrosine-specific protein kinases (PTK's) were first detected in studies of transforming retroviruses. Several of these retrovirally-encoded oncogenes were derived from cellular genes whose products are now known to be intracellular tyrosine kinases thought to act as signaling molecules. Studies of oncogenic intracellular PTK's have demonstrated that if the regulatory restraints are removed by mutation or deletion of key sequences, malignant transformation may ensue (J. Bishop, Leukemia, 2: 199–208, 1988). Multiple receptor tyrosine kinases have also been identified; many play a critical role in the transmembrane transfer of growth and differentiation signals. These receptors are normally activated by soluble or membrane-bound ligand (A. Ullrich & J. Schlessinger, Cell, 61: 203–12, 1990). However, several transforming oncogenes derived from receptor tyrosine kinases have demonstrated that these too can be mutated so as to escape normal control mechanisms. For example, the transforming ability of the c-fms and neu proto-oncogenes can be induced by a single amino acid change in the extracellular or transmembrane domain (M. Roussel et al., Cell, 55: 979–88, 1988; J. Woolford et al., Cell, 55: 965–77, 1988; H. Maguire & M. Greene, Semin Oncol, 16: 148–55, 1989). Additionally, retroviral transduction has created viral oncogenes such as v-erbB, v-kit, and v-sea by a more drastic loss of sequence (H. Kung et al., Dev Biol Stand, 72: 139–144, 1990; P. Besmer et al., Nature, 320: 415–21, 1986; J. Knight et al., Genes Dev, 2: 247–58, 1988). In these cases, a large deletion of the extracellular domain abrogates ligand dependence, resulting in constitutive tyrosine kinase activity.

Another example of extracellular domain deletion during viral transduction was the recently described chicken RPL30 virus which contained a truncated tyrosine kinase, v-ryk (R. Jia et al., J Virol, 66: 5975–87, 1992). The corresponding proto-oncogene was postulated to encode a receptor type tyrosine kinase because the catalytic domain sequence resembled that of other receptor tyrosine kinases, but sequence of the extracellular region was unknown.

SUMMARY OF THE INVENTION

In this application we disclose the cloning of the c-mer protooncogene, a heretofore unknown member of the axl oncogene family. As discussed below, our cDNA was isolated from a B lymphoblastoid λgt11 expression library screened using anti-phosphotyrosine antibodies (H. Earp et al., J Biol Chem, 260: 4351–4356, 1985; H. Earp et al., Proc Natl Acad Sci USA, 81: 2347–2351, 198410, 11). We refer to our human cDNA clone as c-mer, since this gene is expressed in monocytes and tissues of epithelial and reproductive origin.

The extracellular domain of c-mer contains two amino terminal Ig and two membrane proximal fibronectin type III (FNIII) domains, and the kinase contains the sequence KWIAIES. These structural features place our kinase in the axl family of tyrosine kinases (J. O'Bryan et al., Mol Cell Biol, 11: 5016–31, 1991), as noted above. An additional member of the axl family, tyro-3 (C. Lai & G. Lemke, Neuron, 6: 691–704, 1991), has also been reported.

The putative proto-oncogene c-mer is not expressed in freshly isolated lymphocytes, yet c-mer is present in a variety of transformed lymphocyte cell lines. These findings suggest a correlation of altered or inappropriate c-mer expression in certain neoplastic events. This correlation would be similar to that postulated for other cellular proto-oncogenes such as HER2/neu, axl, c-myb, and c-myc which are activated by over-, mis-, or ectopic expression. (C. Bargmann et al., Cell, 45: 649–57, 1986; K. Alitalo et al., Proc Natl Acad Sci USA, 81: 4534–4538, 1984; S. Collins, Nature, 298: 679–681, 1982; C. Little et al., Nature, 306: 194–196, 1983).

Accordingly, a first aspect of the present invention is an isolated DNA encoding a c-mer receptor, particularly a mammalian c-mer which exhibits c-mer protooncogene activity and/or tyrosine kinase activity. More particularly, such DNAs are DNAs selected from the group consisting of: (a) isolated DNA which encodes a human c-mer receptor; (b) isolated DNA which hybridizes to isolated DNA of (a) above and which encodes a c-mer receptor (e.g., isolated DNA which hybridizes to an oligonucleotide that hybridizes to isolated DNA above, which oligonucleotide does not hybridize to isolated DNA encoding the human axl oncogene described in J. O'Bryan et al. (Mol Cell Biol, 11: 5016-31, (1991)) under the same hybridization conditions), and (c) isolated DNA differing from the isolated DNAs of (a) and (b) above in nucleotide sequence due to the degeneracy of the genetic code, and which encodes a c-mer receptor. Recombinant DNA comprising vector DNA and a DNA as described above, along with host cells containing such recombinant DNA and capable of expressing the same, are also disclosed.

A second aspect of the present invention is an isolated and purified c-mer receptor selected from the group consisting of mammalian c-mer receptor proteins and soluble extracellular fragments thereof having c-mer receptor binding activity. More particularly, such receptors are c-mer receptors coded for by a DNA selected from the group consisting of: (a) DNA which encodes a human c-mer receptor; (b) DNA which hybridizes to isolated DNA of (a) above and which encodes a c-mer receptor; (c) DNA differing from the DNAs of (a) and (b) above in nucleotide sequence due to the degeneracy of the genetic code, and which encodes a c-mer receptor; and (d) DNA which encodes a soluble extracellular fragment of a c-mer receptor protein encoded by a DNA of (a), (b), or (c) above, which fragment has c-mer receptor binding activity.

A third aspect of the present invention is a soluble mammalian c-mer receptor which exhibits c-mer receptor binding activity. Such receptors may comprise a mammalian c-mer receptor having a deleted transmembrane region, or the extracellular portion of a mammalian c-mer receptor protein.

A fourth aspect of the present invention is recombinant DNA constructs coding for chimeric proteins, along with the coded-for chimeric proteins. The chimeric protein comprise a c-mer receptor extracellular portion having c-mer receptor binding activity operatively associated an effector portion capable of generating a detectable signal upon binding of a ligand to said c-mer receptor extracellular portion.

C-mer receptor proteins of the instant invention are useful as tyrosine kinases, and DNAs encoding them are useful as intermediates for making such tyrosine kinases. Tyrosine kinases may be used as discussed in section C below.

cDNAs of the instant invention may be used to create receptors or soluble extracellular fractions thereof, as noted above, which are useful to block the action of the receptor ligand in situ to inhibit the growth of a cell, such as a tumor cell, that is being driven by or stimulated to grow by the ligand.

It has been noted that the carboxy-terminal region of the protein of the instant invention, beyond the tyrosine kinase domain, becomes phosphorylated by the tyrosine kinase domain upon activation thereof. The phosphorylated terminal region then serves as a specific binding site or domain for still other proteins. Thus, the intracellular domain may be provided, in soluble form or in the form of the total protein, to isolate intracellular proteins or ligands that are part of the c-mer signalling pathway.

It is particularly noteworthy that c-mer DNA expression is found in tumor tissue (peripheral T and B cell lines) and in human tumor samples, but not in normal cell lines. Therefore, the instant invention has diagnostic and prognostic utility as discussed above for diseases such as leukemia and prostate cancer.

Thus, a further aspect of the present invention are antibodies, such as monoclonal antibodies, which specifically binds to the c-mer receptor, along with hybridomas for making such monoclonal antibodies.

A still further aspect of the present invention is an assay for detecting, prognosing or diagnosing a tumor or cancer such as leukemia or prostate cancer. The assay comprises detecting the amplification of c-mer DNA in a cell or the overexpression of the c-mer receptor protein in a cell (e.g., by the missexpression of the c-mer receptor protein in a cell; i.e., the expression of the receptor protein in a cell where it is not ordinarily expressed. Detecting the presence of such DNA amplification or protein overexpression indicates the presence of a cancer cell, or indicates that such cell is likely to develop into a cancer cell. The assay may be carried out by first, contacting cells to antibodies capable of specifically binding the extracellular domain of the c-mer receptor, and then determining the extent of binding of said antibodies to said cells. Alternatively, the assay may be carried out by contacting to cells an oligonucleotide that binds selectively to DNA encoding the c-mer receptor, and then determining the extent of binding of such oligonucleotides to the DNA of those cells.

The foregoing and other objects and aspects of the present invention are explained in detail in the drawings herein and the specification set forth below.

BRIEF DESCRIPTION OF THE DRAWING

The Figure shows the structure of the c-mer cDNA, with the overall domain structure and the location of various oligonucleotides indicated. The insert created by alternative splicing is shown with the location of oligonucleotide 50R, and the internal stop is demarcated by a (*) therein.

DETAILED DESCRIPTION OF THE INVENTION

Figure 1:
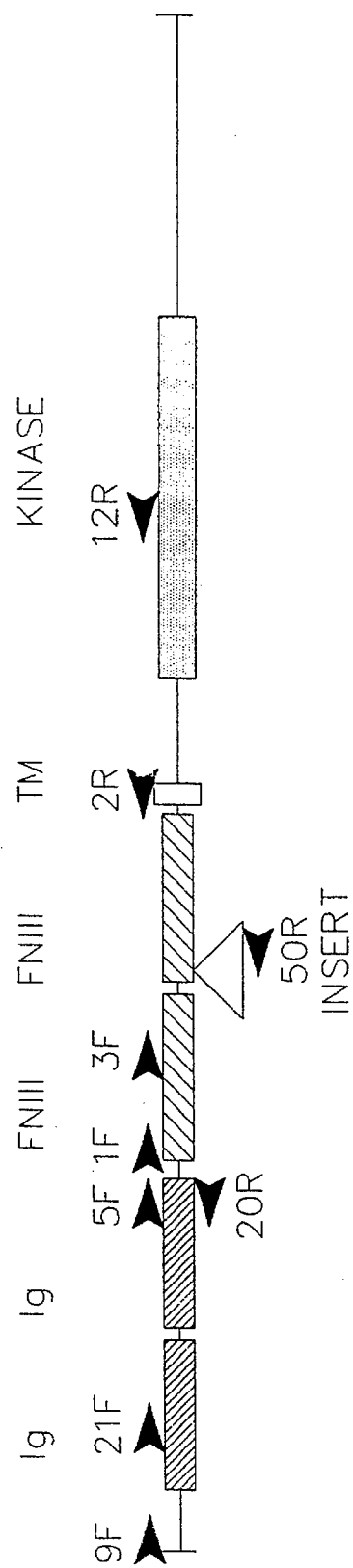

Amino acid sequences disclosed herein are presented in the amino to carboxy direction, from left to right. The amino and carboxy groups are not presented in the sequence.

Nucleotide sequences are presented herein by single strand only, in the 5' to 3' direction, from left to right.

The term "protooncogene", as used herein, refers to a genetic sequence whose expression or overexpression within a cell induces that cell to become converted from a normal cell into a tumor cell.

A. Genetic Engineering Techniques

The production of cloned genes, recombinant DNA, vectors, transformed host cells, proteins and protein fragments by genetic engineering is well known. See, e.g., U.S. Pat. No. 4,761,371 to Bell et al. at Col. 6 line 3 to Col. 9 line 65; U.S. Pat. No. 4,877,729 to Clark et al. at Col. 4 line 38 to Col. 7 line 6; U.S. Pat. No. 4,912,038 to Schilling at Col. 3 line 26 to Col. 14 line 12; and U.S. Pat. No. 4,879,224 to Wallner at Col. 6 line 8 to Col. 8 line 59.

A vector is a replicable DNA construct. Vectors are used herein either to amplify DNA encoding c-mer and/or to express c-mer. An expression vector is a replicable DNA construct in which a c-mer protooncogene is operably linked to suitable control sequences capable of effecting the expression of c-mer in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation.

Amplification vectors do not require expression control domains. All that is needed is the ability to replicate in a host, usually conferred by an origin of replication, and a selection gene to facilitate recognition of transformants.

Vectors comprise plasmids, viruses (e.g., adenovirus, cytomegalovirus), phage, and integratable DNA fragments (i.e., fragments integratable into the host genome by recombination). The vector replicates and functions independently of the host genome, or may, in some instances, integrate into the genome itself. Expression vectors should contain a promoter and RNA binding sites which are operably linked to the gene to be expressed and are operable in the host organism.

DNA regions are operably linked or operably associated when they are functionally related to each other. For example, a promoter is operably linked to a coding sequence if it controls the transcription of the sequence; or a ribosome binding site is operably linked to a coding sequence if it is positioned so as to permit translation.

Transformed host cells are cells which have been transformed or transfected with vectors containing a c-mer protooncogene constructed using recombinant DNA techniques. Transformed host cells ordinarily express c-mer, but host cells transformed for purposes of cloning or amplifying c-mer protooncogene DNA need not express c-mer.

Suitable host cells include prokaryote, yeast or higher eukaryotic cells such as mammalian cells and insect cells. Cells derived from multicellular organisms are a particularly suitable host for synthesis of the c-mer protooncogene receptor by recombinant means, and mammalian cells are particularly preferred. Propagation of such cells in cell culture has become a routine procedure (Tissue Culture, Academic Press, Kruse and Patterson, editors (1973)).

Examples of useful host cell lines are VERO and HeLa cells, Chinese hamster ovary (CHO) cell lines, and WI138, BHK, COS-7, CV, and MDCK cell lines. Expression vectors for such cells ordinarily include (if necessary) an origin of replication, a promoter located upstream from the c-mer protooncogene to be expressed and operatively associated therewith, along with a ribosome binding site, an RNA splice site (if intron-containing genomic DNA is used), a polyadenylation site, and a transcriptional termination sequence.

The transcriptional and translational control sequences in expression vectors to be used in transforming vertebrate cells are often provided by viral sources. For example, commonly used promoters are derived from polyoma, Adenovirus 2, and Simian Virus 40 (SV40). See, e.g., U.S. Pat. No. 4,599,308.

An origin of replication may be provided either by construction of the vector to include an exogenous origin, such as may be derived from SV 40 or other viral (e.g. Polyoma, Adenovirus, VSV, or BPV) source, or may be provided by the host cell chromosomal replication mechanism. If the vector is integrated into the host cell chromosome, the latter is often sufficient.

Rather than using vectors which contain viral origins of replication, one can transform mammalian cells by the method of cotransformation with a selectable marker and the c-mer protooncogene. Examples of suitable selectable markers are dihydrofolate reductase (DHFR) or thymidine kinase. This method is further described in U.S. Pat. No. 4,399,216 (Applicant specifically intends that the disclosure of all patent references cited herein be incorporated herein by reference).

Other methods suitable for adaptation to the expression of a c-mer protooncogene in recombinant vertebrate cell culture include those described in M-J. Gething et al., *Nature* 293, 620 (1981); N. Mantei et al., *Nature* 281, 40; A. Levinson et al., EPO Application Nos. 117,060A and 117,058A.

Host cells such as insect cells (e.g., cultured *Spodoptera frugiperda* cells) and expression vectors such as the baculovirus expression vector (e.g., vectors derived from *Autographa californica* MNPV, *Trichoplusia ni* MNPV, *Rachiplusia ou* MNPV, or *Galleria ou* MNPV) may be employed in carrying out the present invention, as described in U.S. Pat. Nos. 4,745,051 and 4,879,236 to Smith et al. In general, a baculovirus expression vector comprises a baculovirus genome containing the gene to be expressed inserted into the polyhedrin gene at a position ranging from the polyhedrin transcriptional start signal to the ATG start site and under the transcriptional control of a baculovirus polyhedrin promoter.

Prokaryote host cells include gram negative or gram positive organisms, for example *Escherichia coli* (*E. coli*) or Bacilli. Higher eukaryotic cells include established cell lines of mammalian origin as described below. Exemplary host cells are *E. coli* W3110 (ATCC 27,325), *E. coli* B, *E. coli* X1776 (ATCC 31,537), *E. coli* 294 (ATCC 31,446). A broad variety of suitable prokaryotic and microbial vectors are available. *E. coli* is typically transformed using pBR322. Promoters most commonly used in recombinant microbial expression vectors include the beta-lactamase (penicillinase) and lactose promoter systems (Chang et al., *Nature* 275, 615 (1978); and Goeddel et al., *Nature* 281, 544 (1979)), a tryptophan (trp) promoter system (Goeddel et al., *Nucleic Acids Res.* 8, 4057 (1980) and EPO App. Publ. No. 36,776) and the tac promoter (H. De Boer et al., *Proc. Natl. Acad. Sci. USA* 80, 21 (1983)). The promoter and Shine-Dalgarno sequence (for prokaryotic host expression) are operably linked to the c-mer protooncogene, i.e., they are positioned so as to promote transcription of c-mer protooncogene messenger RNA from the DNA.

Eukaryotic microbes such as yeast cultures may also be transformed with c-mer protooncogene vectors. see, e.g., U.S. Pat. No. 4,745,057. *Saccharomyces cerevisiae* is the most commonly used among lower eukaryotic host microorganisms, although a number of other strains are commonly available. Yeast vectors may contain an origin of replication from the 2 micron yeast plasmid or an autonomously replicating sequence (ARS), a promoter, a c-mer protooncogene, sequences for polyadenylation and transcription termination, and a selection gene. An exemplary plasmid is YRp7, (Stinchcomb et al., *Nature* 282, 39 (1979); Kingsman et al., *Gene* 7, 141 (1979); Tschemper et al., *Gene* 10, 157 (1980)). Suitable promoting sequences in yeast vectors include the promoters for metallothionein, 3-phosphoglycerate kinase (Hitzeman et al., *J. Biol. Chem.* 255, 2073 (1980) or other glycolytic enzymes (Hess et al., *J. Adv. Enzyme Reg.* 7, 149 (1968); and Holland et al., *Biochemistry* 17, 4900 (1978)). Suitable vectors and promoters for use in yeast expression are further described in R. Hitzeman et al., EPO Publn. No. 73,657.

B. C-mer Protoncogenes

C-mer protooncogenes of the present invention include those coding for proteins homologous to, and having essentially the same biological properties as, the human c-mer protooncogenes disclosed herein, and particularly the human c-mer protooncogene disclosed herein as SEQ ID NO:1 and encoding the receptor protein given herein SEQ ID NO:2. This definition is intended to encompass natural allelic variations in the c-mer protooncogene. Cloned genes of the present invention can be of any species of origin, including mouse, rat, rabbit, cat, porcine, and human, but are preferably of mammalian origin. Thus, DNAs which hybridize to DNA which encodes human c-mer and which code on expression for a c-mer receptor protein are also an aspect of this invention. Conditions which will permit other DNAs which code on expression for a c-mer receptor protein to hybridize to the DNA of the human c-mer protooncogenes disclosed herein can be determined in accordance with known techniques. For example, hybridization of such sequences may be carried out under conditions of reduced stringency, medium stringency or even stringent conditions (e.g., conditions represented by a wash stringency of 35–40% Formamide with 5× Denhardt's solution, 0.5% SDS and 1× SSPE at 37° C.; conditions represented by a wash stringency of 40–45% Formamide with 5× Denhardt's solution, 0.5% SDS, and 1× SSPE at 42° C.; and conditions represented by a wash stringency of 50% Formamide with 5× Denhardt's solution, 0.5% SDS and 1× SSPE at 42° C., respectively, to DNA encoding the c-mer protooncogene disclosed herein in a standard hybridization assay. See J. Sambrook et al., Molecular Cloning, A Laboratory Manual (2d Ed. 1989)(Cold Spring Harbor Laboratory)). In general, sequences which code for c-mer receptor protein and hybridize to the c-mer protooncogenes disclosed herein will be at least 75% homologous, 85% homologous, and even 95% homologous or more with the sequence of the human c-mer protooncogenes disclosed herein. Further, DNAs which code for c-mer receptor proteins, or sequences which code for a receptor protein coded for by a sequence which hybridizes to the DNAs which code for human c-meroncogenes disclosed herein, but which differ in codon sequence from these due to the degeneracy of the genetic code, are also an aspect of this invention. The degeneracy of the genetic code, which allows different nucleic acid sequences to code for the same protein or peptide, is well known in the literature. See, e.g., U.S. Pat. No. 4,757,006 to Toole et al. at Col. 2, Table 1.

Knowledge of the c-mer nucleotide sequence as disclosed herein can be used to generate hybridization probes which specifically bind to the c-mer gene or mRNA to determine the presence of c-mer gene amplification or overexpression. The hybridization probes may be cDNA fragments or oligonucleotides, and may be labelled with a detectable group as discussed hereinbelow. Pairs of probes which will serve as PCR primers for the c-mer protooncogene or a portion thereof may be used in accordance with the process described in U.S. Pat. Nos. 4,683,202 and 4,683,195.

C. C-mer Receptors and Proteins

As noted above, the present invention provides isolated and purified c-mer receptors, such as mammalian (or more preferably human) c-mer receptor proteins, and soluble extracellular fragments thereof which have c-mer receptor binding activity. Such receptors can be purified from host cells, as described above, which express the same, in accordance with known techniques, or even manufactured synthetically. A specific example of such a receptor is the protein having the amino acid sequence given as SEQ ID NO:2 herein, and the soluble extracellular fragments thereof.

The c-mer receptor proteins disclosed herein have tyrosine kinase activity. Thus, they are useful as tyrosine kinases, and DNAs encoding them are useful as intermediates for making such tyrosine kinases. For example, these tyrosine kinases are useful for phosphorylating proteins to provide a bioassay for phoasphatases. For example, alkaline phosphatase is a commonly used laboratory reagent, and phosphorylated proteins produced with the tyrosine kinases of the present invention are accordingly useful in detecting the presence of alkaline phosphatase in a solution, or in determining the amount thereof in a solution.

The c-mer receptor proteins are of known amino acid sequence as disclosed herein, and hence are useful as molecular weight markers in determining the molecular weights of proteins of unknown structure.

Soluble mammalian c-mer receptors which exhibits c-mer receptor binding activity can be made by deleting the hydrophobic transmembrane region of the native c-mer receptor. By "deletion" is meant removal or alteration of a sufficient portion of the hydrophobic transmembrane domain to render the coded-for receptor soluble in an aqueous solution. In addition, soluble c-mer receptors can be made from the extracellular portion of a mammalian c-mer receptor protein as disclosed herein, with the extracellular portion comprising the portion coded for by the domain 5' to the transmembrane domain of the c-mer protooncogene.

Soluble c-mer receptors may be used in a variety of ways. They may be used for therapeutic purposes, administered to block or stimulate the function of the in situ c-mer protein, along the same lines disclosed in PCT Application No. WO09015870 with respect to the IL-7 receptor. They may be provided in an aqueous solution, solubilzed therein, to screen for c-mer receptor binding ligands, or immobilized on a solid support such as dextrose or silica to provide an affinity column which can be used to bind c-mer receptor binding ligands. The soluble receptor can be labelled with a detectable group such as an alkaline phosphatase in the manner described by J. Flanagan and P. Leder, *Cell* 63, 185–194 (1990), to seek out a membrane-bound ligand for the c-mer receptor in an immunohistochemical procedure. Other detectable groups can be employed, and the term "labelled" is used herein to refer to the conjugating or covalent bonding of any suitable detectable group, including enzymes (e.g., horseradish peroxidase, β-glucuronidase, alkaline phosphatase, and β-D-galactosidase), fluorescent labels (e.g., fluorescein, luciferase), and radiolabels (e.g., $^{14}C$, $^{131}I$, $^{3}H$, $^{32}P$, and $^{35}S$) to the compound being labelled. Techniques for labelling various compounds, including proteins, peptides, and antibodies, are well known. See, e.g., Morrison, *Methods in Enzymology* 32b, 103 (1974); Syvanen et al., *J. Biol. Chem.* 284, 3762 (1973); Bolton and Hunter, *Biochem. J.* 133, 529 (1973).

The c-mer protooncogenes disclosed herein can be used to construct chimeric proteins which are useful for, among other things, detecting the binding of c-mer receptor ligands. Such chimeric proteins can be made with a recombinant DNA construct which codes for the chimeric protein. The construct comprises (a) a c-mer receptor extracellular portion having c-mer receptor binding activity operatively associated with (b) an effector portion capable of generating a detectable signal upon binding of a ligand to the c-mer receptor extracellular portion. Suitable effector portions are the enzymatic domain of a membrane bound kinase, such as the enzymatic portion of an epidermal growth factor receptor. The chimeric protein is expressed in a suitable host cell in accordance with the techniques described above so that, when a c-mer receptor ligand is contacted to the host cell (or a membrane fraction thereof), a detectable signal such as enzymatic activity is generated through activation of the effector portion.

Antibodies which specifically bind to the c-mer receptor (i.e., antibodies which bind to a single antigenic site or epitope on the c-mer receptor) are useful for a variety of diagnostic and therapeutic purposes. Such antibodies may be polyclonal or monoclonal in origin, but are preferably of monoclonal origin. The antibodies are preferably IgG antibodies of any suitable species, such as rat, rabbit, or horse, but are generally of mammalian origin. Fragments of IgG antibodies which retain the ability to specifically bind the c-mer receptor, such as F(ab')$_2$, F(ab'), and Fab fragments, are intended to be encompassed by the term "antibody" herein. The antibodies may be chimeric, as described by M. Walker et al., *Molecular Immunol.* 26, 403 (1989). Preferred are antibodies which specifically bind to the extracellular domain of the c-mer receptor.

Monoclonal antibodies which bind to c-mer are made by culturing a cell or cell line capable of producing the antibody under conditions suitable for the production of the antibody (e.g., by maintaining the cell line in HAT media), and then collecting the antibody from the culture (e.g., by precipitation, ion exchange chromatography, affinity chromatography, or the like). The antibodies may be generated in a hybridoma cell line in the widely used procedure described by G. Kohler and C. Milstein, *Nature* 256, 495 (1975), or may be generated with a recombinant vector in a suitable host cell such as *Escherichia coli* in the manner described by W. Huse et al., Generation of a Large Combinatorial Library of the Immunoglobulin Repertoire in Phage Lambda, *Science* 246, 1275 (1989).

An antibody as described above which is capable of inhibiting c-mer receptor function may be used for therapeutic purposes or in vitro diagnostic purposes, along the lines described in R. Hudziak et al., PCT Appln WO 89/06692. Inhibition can be achieved with an antibody which blocks receptor function (i.e., an antagonist), or with an antibody that stimulates receptor function (i.e., an agonist) through downregulation. Antibodies which specifically bind the extracellular domain of the c-mer receptor may be conjugated to thericin aA chain in the manner described by Vitetta et al., *Science* 238, 1098 (1987).

Assays for detecting c-mer expression on a cell or the extent of expression thereof generally comprise the steps of, first, contacting cells to antibodies capable of specifically binding the c-mer receptor, particularly the extracellular domain of the c-mer receptor, and determining the extend of binding of said antibodies to said cells. The antibody is preferably labelled, as discussed above, to facilitate the detection of binding. Any suitable immunoassay procedure may be employed, such as radioimmunoassay, immunofluorescence, precipitation, agglutination, complement fixation, and enzyme-linked immunosorbent assay. When the cells to be tested remain within the body of a mammal, the antibodies are labelled with a radioactive detectable group and administered to the mammal, and the extent of binding of the antibodies to the cells is observed by external scanning for radioactivity. As discussed above, while any type of antibody may be employed for the foregoing diagnostic purposes, monoclonal antibodies are preferred.

Assays for detecting c-mer DNA or mRNA in a cell, or the extent of amplification thereof, typically involve, first, contacting the cells or extracts of the cells containing nucleic acids therefrom with an oligonucleotide that specifically binds to c-mer DNA or mRNA as given herein (typically under conditions that permit access of the oligonucleotide to intracellular material), and then detecting the presence or absence of binding of the oligonucleotide thereto. Again, any suitable assay format may be employed (see, e.g., U.S. Pat. No. 4,358,535 to Falkow et al.; U.S. Pat. Nos. 4,302,204 to Wahl et al.; 4,994,373 to Stavrianopoulos et al; 4,486,539 to Ranki et al.; 4,563,419 to Ranki et al.; and 4,868,104 to Kurn et al.) (the disclosures of which applicant specifically intends be incorporated herein by reference).

D. C-mer Receptor Ligands

Ligands that bind to the c-mer receptor, whether at the extracellular domain or at the intracellular tyrosine kinase domain, are a further aspect of the present invention. Such ligands may be administered to a cell that expresses the c-mer receptor to stimulate or inhibit the function of that receptor, for example to stimulate or inhibit cell the growth of that cell.

As used herein, the term "ligand" refers to a molecule that is recognized by a particular receptor domain, whether the extracellular ligand receptor domain or the intracellular tyrosine kinase receptor domain of c-mer proteins of the presennt invention. Ligands may be or antagonists that specifically binds to and inhibit the normal activity of the particular protein receptor domain, or agonists that specifically bind to and activate the normal activity of the particular receptor domain.

Thus the term "ligand" includes the natural ligands of the given receptor domain and analogs thereof. As used herein, an "analog" is a chemical compound similar in structure to a first compound, and having either a similar or opposite physiologic action as the first compound. With particular reference to the present invention, ligand analogs are those compounds which, while not having the amino acid sequences of the native ligands, are capable of binding to the given receptor domain. Such analogs may be peptide or non-peptide analogs, including nucleic acid analogs, as described in further detail below.

In protein molecules which interact with a receptor, the interaction between the protein and the receptor must take place at surface-accessible sites in a stable three-dimensional molecule. By arranging the critical binding site residues in an appropriate conformation, peptides which mimic the essential surface features of the intracellular or extracellular receptor domains of the c-mer proteins of the present invention may be designed and synthesized in accordance with known techniques.

Methods for determining peptide three-dimensional structure and analogs thereto are known, and are sometimes referred to as "rational drug design techniques". See, e.g., U.S. Pat. No. 4,833,092 to Geysen; U.S. Pat. No. 4,859,765 to Nestor; U.S. Pat. No. 4,853,871 to Pantoliano; U.S. Pat. No. 4,863,857 to Blalock; (applicants specifically intend that the disclosures of all U.S. Patent references cited herein be incorporated by reference herein in their entirety). See also Waldrop, *Science,* 247, 28029 (1990); Rossmann, *Nature,* 333, 392–393 (1988); Weis et al., *Nature,* 333, 426–431 (1988); James et al., *Science,* 260, 1937 (1993) (development of benzodiazepine peptidomimetic compounds based on the structure and function of tetrapeptide ligands).

Ligands may also be developed by generating a library of molecules, selecting for those molecules which act as ligands for a specified target, and identifying and amplifying the selected ligands. See, e.g., Kohl et al., *Science,* 260, 1934 (1993) (synthesis and screening of tetrapeptides for inhibitors of farnesyl protein transferase, to inhibit ras oncoprotein dependent cell transformation). Techniques for constructing and screening combinatorial libraries of oligomeric biomolecules to identify those that specifically bind to a given receptor protein are known. Suitable oligomers include peptides, oligonucleotides, carbohydrates, nonoligonucleotides (e.g., phosphorothioate oligonucleotides; see *Chem. and Engineering News,* page 20, 7 Feb. 1994) and nonpeptide polymers (see, e.g., "peptoids" of Simon et al., *Proc. Natl. Acad. Sci. USA,* 89, 9367 (1992)). See also U.S. Pat. No. 5,270,170 to Schatz; Scott and Smith, *Science,* 249, 386–390 (1990); Devlin et al., *Science* 249, 404–406 (1990); Edgington, *BIO/Technology,* 11, 285 (1993). Peptide libraries may be synthesized on solid supports, or expressed on the surface of bacteriophage viruses (phage display libraries). Known screening methods may be used by those skilled in the art to screen combinatorial libraries to identify ligands. Techniques are known in the art for screening synthesized molecules to select those with the desired activity, and for labelling the members of the library so that selected active molecules may be identified. See, e.g., Brenner and Lerner, *Proc. Natl. Acad. Sci. USA,* 89, 5381 (1992) (use of genetic tag to label molecules in a combinatorial library); PCT US93/06948 to Berger et al., (use of recombinant cell transformed with viral transactivating element to screen for potential antiviral molecules able to inhibit initiation of viral transcription); Simon et al., *Proc. Natl. Acad. Sci. USA,* 89, 9367, (1992) (generation and screening of "peptoids", oligomeric N-substituted glycines, to identify ligands for biological receptors); U.S. Pat. No. 5,283,173 to Fields et al., (use of genetically altered *Saccharomyces cerevisiae* to screen peptides for interactions).

As used herein, "combinatorial library" refers to collections of diverse oligomeric biomolecules of differing sequence, which can be screened simultaneously for activity as a ligand for a particular target. Combinatorial libraries may also be referred to as "shape libraries", i.e., a population of randomized polymers which are potential ligands. The shape of a molecule refers to those features of a molecule that govern its interactions with other molecules, including Van der Waals, hydrophobic, electrostatic and dynamic.

Nucleic acid molecules may also act as ligands for receptor proteins. See, e.g., Edgington, *BIO/Technology,* 11, 285 (1993). U.S. Pat. No. 5,270,163 to Gold and Tuerk describes a method for identifying nucleic acid ligands for a given target molecule by selecting from a library of RNA molecules with randomized sequences those molecules that bind specifically to the target molecule. A method for the in vitro selection of RNA molecules immunologically cross-reactive with a specific peptide is disclosed in Tsai, Kenan and Keene, *Proc. Natl. Acad. Sci. USA*, 89, 8864 (1992) and Tsai and Keene, *J. Immunology*, 150, 1137 (1993). In the method, an antiserum raised against a peptide is used to select RNA molecules from a library of RNA molecules; selected RNA molecules and the peptide compete for antibody binding, indicating that the RNA epitope functions as a specific inhibitor of the antibody-antigen interaction.

In addition, the modeling of a protein kinase structure using the known structure of other kinases is reported by Knighton et al., *Science*, 258, 130 (1992) (smooth muscle myosin light chain kinase catalytic core modeled using crystallography data of cyclic AMP-dependent protein kinase catalytic subunit and a bound pseudosubstrate inhibitor). See also Marcote et al., *Mol. Cell. Biol.*, 13, 5122 (1993) (crystallography data of cyclic AMP dependent protein kinase used to model Cdc2 protein kinase); Knighton et al., *Science*, 253, 407 (1991); Knighton et al., *Science*, 253, 414 (1991); DeBondt et al., *Nature*, 363, 595 (1993) (crystal structure of human CDK2 kinase determined).

In general, those skilled in the art will appreciate that minor deletions or substitutions may be made to the amino acid sequences of peptides of the present invention without unduly adversely affecting the activity thereof. Thus, peptides containing such deletions or substitutions are a further aspect of the present invention. In peptides containing substitutions or replacements of amino acids, one or more amino acids of a peptide sequence may be replaced by one or more other amino acids wherein such replacement does not affect the function of that sequence. Such changes can be guided by known similarities between amino acids in physical features such as charge density, hydrophobicity/hydrophilicity, size and configuration, so that amino acids are substituted with other amino acids having essentially the same functional properties. For example: Ala may be replaced with Val or Ser; Val may be replaced with Ala, Leu, Met, or Ile, preferably Ala or Leu; Leu may be replaced with Ala, Val or Ile, preferably Val or Ile; Gly may be replaced with Pro or Cys, preferably Pro; Pro may be replaced with Gly, Cys, Ser, or Met, preferably Gly, Cys, or Ser; Cys may be replaced with Gly, Pro, Ser, or Met, preferably Pro or Met; Met may be replaced with Pro or Cys, preferably Cys; His may be replaced with Phe or Gln, preferably Phe; Phe may be replaced with His, Tyr, or Trp, preferably His or Tyr; Tyr may be replaced with His, Phe or Trp, preferably Phe or Trp; Trp may be replaced with Phe or Tyr, preferably Tyr; Asn may be replaced with Gln or Ser, preferably Gln; Gln may be replaced with His, Lys, Glu, Asn, or Ser, preferably Asn or Ser; Ser may be replaced with Gln, Thr, Pro, Cys or Ala; Thr may be replaced with Gln or Ser, preferably Ser; Lys may be replaced with Gln or Arg; Arg may be replaced with Lys, Asp or Glu, preferably Lys or Glu; Asp may be replaced with Lys, Arg, or Glu, preferably Arg or Glu; and Glu may be replaced with Arg or Asp, preferably Asp. Once made, changes can be routinely screened to determine their effects on function with enzymes.

Non-peptide mimetics of the peptides of the present invention are also an aspect of this invention. Non-protein drug design may be carried out using computer graphic modeling to design non-peptide, organic molecules able to bind to the receptors of the invention. See, e.g., Knight, *BIO/Technology*, 8, 105 (1990). Itzstein et al, *Nature*, 363, 418 (1993) (peptidomimetic inhibitors of influenza virus enzyme, sialidase). Itzstein et al modeled the crystal structure of the sialidase receptor protein using data from x-ray crystallography studies and developed an inhibitor that would attach to active sites of the model; the use of nuclear magnetic resonance (NMR) data for modeling is also known in the art. See also Lam et al, *Science*, 263, 380 (January 1994).

The present invention is explained in greater detail in the following non-limiting examples.

Examples

I. MATERIALS AND METHODS

Library screening. Initial c-mer cDNA clones were isolated by probing a B lymphoblastoid λgt11 expression library (RPMI 4265; Clontech) with rabbit polyclonal anti-phosphotyrosine antisera (B. McCune & H. Earp, J Biol Chem, 264: 15501–7, 1989). Briefly, 1×10⁶ clones were plated on twenty 150 mm LB agar plates, grown for two hours at 42° C., then covered with nitrocellulose filters previously soaked with 10 mM isopropyl-β-D-thiogalactoside (IPTG). The plates were then grown for two hours at 42° C., followed by five hours at 37° C. The filters were removed, air dried 15 minutes, washed in RB (10 mM Tris pH 7.2, 150 mM NaCl) and blocked overnight in RB plus 3% BSA (BMB). The filters were probed for two hours at room temperature with polyclonal anti-phosphotyrosine antisera, followed by a one hour incubation with $^{125}$I Staphylococcus protein A (Amersham). Positive phage were plaque purified, the inserts amplified by PCR with insertion of EcoRI restriction sites, and then subcloned into pBluescript II (Stratagene). Two overlapping clones were identified, but neither contained a full-length transcript. To obtain new 5' sequence, oligonucleotides were constructed to span 450 bp of the 5' end of the larger of the two existing clones TK-8 The FIGURE, oligonucleotides 3F to 2R). After identification of a larger clone, new probes were constructed from the new 5' sequence (21F to 20R, Fig.). The probes were generated by PCR incorporation of $^{32}$P dCTP, with unincorporated probe removed by 1 ml Sephadex G-50 spin column centrifugation. cDNA libraries were constructed with peripheral blood monocytes from normal donors and normal human prostate tissue with the Stratagene l-Zap II cDNA construction kit, packaged with GIGAPACK GOLD™, and probed as per manufacturers instructions Positive clones were plaque purified and excised with R408 helper phage (Stratagene). Genomic clones were isolated from a l-FIX II human placental genomic library (Stratagene). The genomic library was plated, lifted, and probed as per the manufacturers instructions with random primed probes (Prime-It II, Stratagene) representing the regions between oligonucleotides 3F to 12R and 21F to 20R (Fig.). Dideoxy sequencing was performed with the USB Sequenase II sequencing kit, utilizing $^{35}$S dATP (Amersham).

RNA Blot Analysis. Human multiple tissue Northern blots (Clontech) were probed as per the manufacturer's instructions. The c-mer probe was identical to the genomic library probe which spanned oligonucleotides 3F to 12R (Fig.). The amount of RNA present was assessed by sequential probing for human β-actin and cyclophilin.

Preparation of peripheral blood cell populations and bone marrow mononuclear cells. Mononuclear cells were isolated from peripheral blood of two healthy donors using Histopaque 1077 (Sigma). Monocytes were separated from lymphocytes using two different methods: (1) adherence to plastic for 40 minutes or (2) flow cytometry using an EPICS V system (Coulter) with appropriates light scatter gates for monocytes. T cells (CD3⁺/CD19⁻) and B cells (CD3⁻/CD19⁺) were purified by flow cytometry from peripheral blood mononuclear cells with appropriate light scatter gates for lymphocytes. As a confirmation, monoclonal antibodies against CD4 and CD8 were used to purify T cells (CD4$^+$ and/or CD8$^+$) and B cells (CD4$^-$/CD8$^-$). FACS reanalysis of sorted cells revealed a suspension purity of greater than 98% for all samples with the exception of the CD4$^+$/CD8$^+$ population, which had a purity of 66% (data not shown). Following Histopaque treatment, the RBC/granulocyte pellet was washed several times with a RBC lysing solution (0.1555M NH$_4$Cl, 0.01M KHCO$_3$ pH 7.0, and 0.1 mM Na$_2$EDTA) to yield purified granulocytes. The bone marrow mononuclear cells were prepared by Ficoll-Paque (Pharmacia) treatment of a bone marrow aspirate from a healthy transplant donor.

Cell lines. The cell lines and their lineages used in this study are summarized in TABLE 1 and TABLE 2. All cell lines were obtained from the American Type Culture Collection unless otherwise indicated. The following cell lines or total cellular RNA were kindly provided by the investigators as noted: PEER and HPB ALL (Dr. John Winfield); UT-7 (Dr. Norio Komatsu); SW480, HT29, LOX, and KB (Dr. Judy Varner); and MCF-7 and K-562 (Dr. Edison Liu). All cell lines were maintained in standard tissue culture conditions. T cell clones C11 and C41 are two human tetanus specific CD4$^+$T cell clones (supplied by Dr. Werner Pichler). Approximately 5×10$^6$ cells from each cell culture were resuspended in a lysing solution (4M guanidinium isothiocyanate, 25 mM sodium citrate pH 7.0, 0.5% sarcosyl, and 0.1M 2-mercaptoethanol) and total RNA was isolated by the acid phenol procedure (P. Chomczynski & N. Sacchi, Anal Biochem, 162: 156–9, 1987). In the TPA induction experiments U-937 and K-562 cells were grown as stated previously. Cells were treated for 72 hours with 100 nM TPA (BMB).

RT-PCR analysis of c-mer expression. The first strand cDNA was prepared using Moloney murine leukemia virus reverse transcriptase in RT buffer (50 mM Tris-HCl pH 8.3, 75 mM KCl, 10 mM DTT, and 3 mM MgCl$_2$), 15 units of RNA guard (Pharmacia), 10 pmoles of random hexamers, and 1.25 mM of each dNTP in a 20 ml reaction. The volume of the cDNA was adjusted to 25–60 ml with TE following first strand synthesis. Five microliters of the first strand cDNA was amplified in a 50 ml volume of PCR buffer (10 mM Tris-HCl pH 9.0, 50 mM KCl, 1.5 mM MgCl$_2$, 0.01% gelatin, and 0.1% Triton X-100), 0.2 mM of each dNTP, 50 pmoles of each primer, and 2.5 units of Taq DNA polymerase (GIBCO BRL). To test for the integrity of the RNA samples and for template standardization, amplification by PCR using actin primers (HACA-1F and HACA-1R) was performed under the following conditions: 5 min at 94° C., 1 min at 55° C., and 2 min at 72° C. (1 cycle), 1 min at 94° C., 1 min at 55° C., and 2 min at 72° C. (22 cycles), and 1 min at 94° C., 1 min at 55° C., and 10 min at 72° C. (1 cycle). The expression of c-mer in the samples was analyzed using the primers 3F and 2R (FIG. 1), which were designed to amplify c-mer in a region of the extracellular domain in which there is sequence divergence from axl. For c-mer amplification in cell lines and freshly isolated hematopoietic populations, 35 cycles were performed with an annealing temperature of 62° C. The cycle number was decreased to 32 cycles to more accurately demonstrate relative levels of c-mer in the cell lines K-562 and U-937 with and without TPA treatment (data not shown). PCR amplification specific for the alternatively spliced isoform containing the 52 bp insert was performed with the primers 1F and 50R at an annealing temperature of 55° C. for 40 cycles. Each PCR reaction contained a reverse transcriptase negative control, a no template control, and a positive control (i.e., peripheral blood mononuclear cells). The sequence of the primers is as follows: (HACA-1F) CCTTCCTGGGCATGGAGTCCT (SEQ ID NO:3); (HACA-1R) GGAGCAATGATCT-TGATCTTC (SEQ ID NO:4); (3F) CACCTCTGCCTTAC-CACATCT (SEQ ID NO:5), and (2R) ATCCACAAAAG-CAGCCAAAGA (SEQ ID NO:6); (1F) AAGTCAGCATCCGTAACAGCA (SEQ ID NO:7); and (50R) GCAAAGAGGAGTCAACAGTAG (SEQ ID NO:8). The PCR products were analyzed by electrophoresis of 10 ml of each reaction on a 1.0% or 1.5% agarose gel containing ethidium bromide.

Sequencing of PCR products. The PCR amplified products were purified by Elu-Quick DNA purification kit (Schleicher and Schuell) according to the manufacturer's instructions. The DNA was then sequenced by two different methods: (1) the PCR product was directly sequenced using Taq polymerase (ds DNA cycle sequencing system; GIBCO BRL) and (2) the PCR product was cloned with the TA cloning kit (Invitrogen) and sequenced with modified T7 polymerase (Sequenase; United States Biochemical). Both strands of the DNA were sequenced for nucleotide confirmation.

II. RESULTS

Cloning and sequencing of c-mer. The original c-mer cDNA was cloned by functional screening of a human B lymphoblastoid λgt11 expression library with polyclonal anti-phosphotyrosine antisera. Along with the previously characterized tyrosine kinase fyn, this screen identified two independent clones of a single novel tyrosine kinase, c-mer. The largest of these clones contained an open reading frame (ORF) encoding a putative transmembrane segment, tyrosine kinase domain, and complete carboxyl terminus. Both clones were truncated at the 5' end, and the smaller clone was a subset of the larger. A 5' probe was constructed (between oligonucleotides 3F and 2R, Fig.) and used to screen other cDNA libraries. Six clones were obtained from screening two independent monocyte cDNA libraries, one of which contained 298 bp of new 5' sequence. New oligonucleotides were synthesized (21F and 20R) and used to make a probe to screen monocyte, prostate and Jurkat cDNA libraries without finding new 5' sequence. Finally, we screened a human placental genomic library with two random primed probes of c-mer, segments 3F to 12R and 21F to 20R (Fig.), and identified 37 positive clones. The genomic clones were subsequently mapped, and five overlapping clones spanning the entire coding region were subcloned into pBSII (Stratagene) for further analysis. Sequencing of the most 5' genomic clone revealed a splice junction at base 578 of the reported sequence, with an open reading frame extending in the 5' direction. A 5' RACE reaction was used to finish cloning the 5' coding region of the mRNA. RACE-ready human peripheral blood lymphocyte cDNA was used. Multiple sequencing reactions confirmed the sequence. An initiation methionine in the context of a canonical Kozak sequence was found at the beginning of a hydrophobic leader sequence.

Another interesting characteristic of the sequence is an internal polyadenylation signal which could be used in transcription of the truncated product predicted to occur in the alternatively spliced isoform. This would be similar to the internal polyadenylation signal which has been shown to occur in the chicken growth hormone receptor (E. Oldham et al., Mol Endocrinol, 7: 1379–1390, 1993.). Finally, the sequence contains a frame-closing stop codon (and multiple stops in all other frames) with a consensus polyadenylation signal 372 bp downstream.

Analysis of putative c-mer protein structure. The entire ORF for c-mer encodes a 999 amino acid polypeptide, including the hydrophobic leader sequence. Comparison of the amino acid sequence to GenBank (S. Altschul et al., J Mol Biol, 215: 403–410, 1990) suggests that c-mer is a possible cellular homologue of the viral oncogene v-ryk, with an 83% amino acid similarity (71% identity) across the segment contained in the virus (data not shown). The similarity in the kinase domain was even higher (91% similarity, 84% identity). The similarity between v-ryk and axl, which is the next closest family member, is clearly lower (82% similarity, 68% identity). Among human sequences c-mer is most similar to axl (64% similarity, 44% identity). Other similarities to axl include a relatively hydrophilic leader sequence and the consensus motif KWIAIES (aa 750–756). Furthermore, the extracellular region of c-mer contains the same motifs as the axl family, including two amino-terminal Ig domains (aa 76 to 168 and 184 to 254) and two membrane proximal FNIII domains (aa 269 to 357 and 360 to 465). The extracellular domain also possesses 13 potential N-linked glycosylation sites (NxS/T), indicating that the mature protein may be heavily glycosylated. Hydropathy analysis (M. Gribskov et al., Nucleic Acids Res, 14: 327–34, 1986) indicates a potential transmembrane segment of up to 25 amino acids (aa 485 to 510). The intracellular region has a consensus tyrosine kinase domain with the signature motif GxGxxG (aa 579–584), the invariant ATP-binding lysine (aa 604), and the tyrosine-specific kinase motifs HRDLAARN (aa 706–713) (S. Hanks et al., Science, 241: 42–52, 1988). At least three potential tyrosine phosphorylation sites are located in the intracellular region (R. Pearson & B. Kemp, Methods Enzymol, 200: 62–81, 1991), including a consensus PI-3 kinase p85 regulatory subunit binding site YXXM (L. Cantley et al., Cell, 64: 281–302, 1991).

Expression of c-mer. Detectable amounts of c-mer were found in peripheral blood mononuclear cells, bone marrow mononuclear cells, and monocytes. In contrast, no c-mer expression was detected by RT-PCR in granulocytes or in lymphocyte populations separated by flow cytometry from freshly isolated peripheral blood (data not shown). The negative expression in lymphocytes was confirmed by two independent cell sorting experiments. In the first cell sort, monoclonal antibodies against the antigens CD3 and CD19 were used to obtain T cells (CD3$^+$/CD19$^-$) and B cells (CD3$^-$/CD19$^+$). The second cell sort utilized monoclonal antibodies against CD4 and CD8 to prepare T cells (CD4$^+$ and/or CD8$^+$) and B cells (CD4$^-$/CD8$^-$) from a second healthy donor. None of these lymphocyte populations exhibited significant c-mer expression.

Tissue analysis of c-mer expression revealed that a 4.4 kb message was highly expressed in testis, ovary, prostate, lung and kidney, with lower expression in spleen, peripheral blood leukocyte, placenta, thymus, small intestine, colon and liver (data not shown). There was no detectable expression in heart, brain, or skeletal muscle. A larger transcript of unknown significance was also detected in testis, ovary, and colon. We probed 2.0 μg of poly A$^+$ mRNA from various tissues with an 1127 bp probe corresponding to oligonucleotides 3F to 12R of c-mer (Fig.) This region includes minimal conserved kinase domain sequence, and therefore is unlikely to hybridize nonspecifically to other tyrosine kinases. The amount and quality of RNA on the Northern blots was assessed by probing for cyclophilin (P. Danielson et al., DNA, 7: 261–7, 1988) and β-actin.

An extensive analysis of 24 cell lines from different tissue sources and two T cell clones by RT-PCR indicates that c-mer is expressed in a spectrum of cell lines of hematopoietic, epithelial, and mesenchymal origin (TABLE 1 and TABLE 2). The high level of expression in the lung carcinoma line A549 is consistent with the high amount of detectable transcript in normal lung. Furthermore, high expression of c-mer in the monocyte cell line U-937 is reflective of the significant amount observed in freshly isolated monocytes. In contrast to these parallels between cell lines and tissues, there is significant expression of c-mer in all of the T-ALL (T cell acute lymphocytic leukemia) cell lines studied. This is intriguing since c-mer is not detected in T cell clones which were generated from a healthy donor (data not shown) or in freshly isolated lymphocytes from normal donors (data not shown). Furthermore, a similar analysis using axl specific primers demonstrates that axl is not expressed in any of the T-ALL cell lines (data not shown). No c-mer expression was found in the cell lines HL-60, SW480, or HeLa (TABLE 1 and TABLE 2).

TABLE 1

Summary of Relative Levels of c-mer expression in Hematopoietic Cells by RT-PCR.

| T lymphocyte, leukemia | |
|---|---|
| (1) CCRF-CEM | + |
| (2) CCRF-HSB-2 | ++ |
| (3) JURKAT, clone E6-1 | ++ |
| (4) HPB-ALL | ++ |
| (5) PEER | +++ |
| (6) MOLT-4 | + |
| T lymphocyte clones | |
| (7) C11 | − |
| (8) C41 | − |
| B lymphocyte, Burkitt's lymphoma | |
| (9) Raji | + |
| (10) Daudi | + |
| CML blast | |
| (11) K-562 | +++ |
| Promyelocytic leukemia | |
| (12) HL-60 | |
| Monocytic leukemia/lymphoma | |
| (13) THP-1 | + |
| (14) U-937 | +++ |
| Megakaryoblastic leukemia | |
| (15) UT-7 | +++ |
| Primary hematopoietic cells | |
| (27) PBMC | ++ |
| (28) Monocytes | ++ |

TABLE 2

Summary of relative levels of c-mer Expression by RT-PCR: Other Cell Lineages.

| Colon carcinoma | |
|---|---|
| (16) SW480 | − |
| (17) HT-29 | ++ |
| Lung carcinoma | |
| (18) A549 | +++ |
| Breast carcinoma | |
| (19) MCF7 | + |
| Glioblastoma | |
| (20) U-138 MG | + |

TABLE 2-continued

Summary of relative levels of c-mer Expression by RT-PCR: Other Cell Lineages.

Cervical carcinoma

| | |
|---|---|
| (21) HeLa | − |

Epidermoid carcinoma

| | |
|---|---|
| (22) A431 | ++ |
| (23) KB | + |

Bladder carcinoma

| | |
|---|---|
| (24) 5637 | + |

Normal human fibroblast

| | |
|---|---|
| (25) WI-38 | + |
| (26) IMR-90 | + |

Presence of an alternative splicing product. The initial analysis of c-mer in hematopoietic cells and cell lines indicated the presence of two different PCR products which were consistently amplified in some cell lines and monocytes from peripheral blood (data not shown). One product was the predicted size of 526 bp and another was approximately 50 bp larger. After Southern transfer of the PCR products to a nylon membrane, both bands were shown to hybridize with an internal oligonucleotide (data not shown). The sequence of the two PCR products with both Taq and T7 polymerases suggested that the larger band was an alternative splicing product containing a 52 bp insertion. Use of the 50R primer, designed to be specific for the insert, in conjunction with a primer approximately 300 bp upstream (1F) demonstrated that a portion of the larger isoform could be selectively amplified from first strand cDNA by RT-PCR. Although total RNA was used in these experiments, similar results were obtained when poly $A^+$ mRNA was used as template for the first strand cDNA synthesis. This strongly supports the existence of this RNA isoform and makes it unlikely that it is either a PCR artifact or an incompletely processed message. The 52 bp insert contains an in frame stop codon within the sequence insertion. If no other modifications were made upstream of this insertion, the resulting protein product would contain the two Ig domains and one FNIII domain. Since the protein would not contain the transmembrane domain sequence, this alternatively spliced product may be secreted. Even if sequence modifications (i.e., insertions or deletions of other exons) did occur in this larger isoform outside of the region amplified by PCR, the net result would not be altered since stop codons exist on both sides of the insertion sequence in the two reading frames that are not employed in generating the full length protein. The transcript for this isoform may utilize the internal polyadenylation site, resulting in a shortened transcript encoding a secreted form of c-mer. This alternative isoform is not likely to be the larger transcript detected in the Northern blot (data not shown).

Effect of TPA treatment on c-mer expression in the cell lines K-562 and U-937. K-562 is a CML blast cell line, which differentiates into a megakaryocytic phenotype when treated with TPA (R. Alitalo et al., EMBO J, 6: 1213-8, 1987). U-937 is an undifferentiated leukemia line which can be differentiated into a monocyte-like phenotype by TPA treatment (D. Ways et al., Cancer Res, 47: 3344–50, 1987). Prior to TPA treatment, both of these cell lines express relatively high levels of c-mer (data not shown); therefore, in the TPA induction experiment the PCR cycle number was reduced by several cycles to maintain the linearity of amplification, more accurately demonstrating the relative levels of c-mer expression. Both K-562 and U-937 showed significantly increased expression of c-mer after prolonged TPA treatment (data not shown).

III. DISCUSSION

The detection of an alteratively spliced product in c-mer is not surprising since other tyrosine kinase receptors such as axl (J. O'Bryan et al., Mol Cell Biol, 11: 5016–31, 1991), FGF receptor (T. Miki et al., Proc Natl Acad Sci USA, 89: 246–50, 1992), insulin receptor (S. Seino & G. Bell, Biochem Biophys Res Commun, 159: 312-6, 1989.), and EGF receptor (L. Petch et al., Mol Cell Biol, 10: 2973–82, 1990) undergo alternative splicing. The alternative splicing isoform of c-mer, containing the 52 bp insertion (CTTTCAAATATGTGTTGAAATCTCTCTTCTACTGTTGACT CCTCTTTGCCTT (SEQ ID NO:9)), may also encode a secreted protein since the insert contains an in frame stop codon within the insertion sequence. This mechanism of producing soluble receptors by inserting an exon coding for polypeptide chain termination prior to the transmembrane domain is also employed by the IL-5 receptor α (J. Tavernier et al., Proc Natl Acad Sci, USA, 89: 7041-5, 1992).

Comparison of the expression pattern of c-mer and axl is instructive. Neither c-mer nor axl is detected in granulocytes or resting lymphocytes from peripheral blood. Axl was isolated from neoplastic CML cells. However, axl is not found in the neoplastic T and B lymphoblastoid cell lines that clearly express c-mer (TABLE 1 and TABLE 2). The fact that axl is not expressed in these cells underscores the potential biologic differences between these two closely related kinases. Expression of c-mer in neoplastic but not mature resting lymphocytes is of interest and indicates a role in, or at least a correlation with, the neoplastic progression of some leukemias and lymphomas.

The foregoing is illustrative of the present invention, and is not to be construed as limiting thereof. The invention is defined by the following claims, with equivalents of the claims to be included therein.

---

That which is claimed is:

1. An isolated DNA molecule encoding a c-mer receptor which has tyrosine kinase activity, said DNA molecule selected from the group consisting of:
 (a) isolated DNA which encodes the human c-mer protooncogene and has the nucleotide sequence of SEQ ID NO:1;
 (b) isolated natural DNA which hybridizes to isolated DNA of (a) above under conditions represented by a wash stringency of 40% Formamide with 5× Denhardt's solution, 0.5% SDS and 1× SSPE at 42° C. and which encodes a c-mer receptor having tyrosine kinase activity; and
 (c) isolated DNA differing from the isolated DNAs of (a) and (b) above in nucleotide sequence due to the degeneracy of the genetic code, and which encodes a c-mer receptor having tyrosine kinase activity.

2. An isolated DNA molecule according to claim 1 that encodes a mammalian c-mer receptor protein.

3. An isolated DNA molecule according to claim 1 that encodes a human c-mer receptor protein.

4. A recombinant DNA molecule having vector DNA and a DNA according to claim 1.

5. A recombinant DNA molecule according to claim 4, wherein said vector DNA comprises a vector selected from the group consisting of plasmids, adenoviruses, and cytomegaloviruses.

6. A recombinant DNA molecule according to claim 4, wherein said vector DNA comprises a baculovirus vector.

7. A host cell containing a recombinant DNA molecule of claim 4 and capable of expressing the encoded protein.

8. A host cell according to claim 7, wherein said host cell is a mammalian cell.

9. A host cell according to claim 7, wherein said host cell is selected from the group consisting of baby hamster kidney cells, mouse cells, human embryo cells, and chinese hamster ovary cells.

10. A host cell according to claim 7, wherein said host cell is an insect cell.

11. A recombinant DNA molecule coding for a chimeric protein comprising a c-mer receptor extracellular portion having c-mer receptor binding activity operatively associated with an effector portion capable of generating a detectable signal upon binding of a ligand to said c-mer receptor extracellular portion;
 and wherein said c-mer receptor extracellular portion is an extracellular portion of a c-mer receptor encoded by an isolated DNA molecule according to claim 1.

12. A recombinant DNA molecule according to claim 11, wherein said effector portion comprises the enzymatic domain of a membrane bound kinase.

13. A recombinant DNA molecule according to claim 11, wherein said effector portion comprises the enzymatic domain of an epidermal growth factor receptor.

14. An isolated DNA molecule encoding a c-mer receptor protein which has tyrosine kinase activity, said c-mer receptor protein having the amino acid sequence given herein as SEQ ID NO:2.

15. An isolated DNA molecule according to claim 14 having the nucleotide sequence given herein as SEQ ID NO:1.

16. A recombinant DNA molecule having vector DNA and a DNA according to claim 14.

17. A recombinant DNA molecule according to claim 16, wherein said vector DNA comprises a vector selected from the group consisting of plasmids, adenoviruses, and cytomegaloviruses.

18. A recombinant DNA molecule according to claim 16, wherein said vector DNA comprises a baculovirus vector.

19. A host cell containing a recombinant DNA molecule of claim 16 and capable of expressing the encoded protein.

20. A host cell according to claim 19, wherein said host cell is a mammalian cell.

21. A host cell according to claim 19, wherein said host cell is selected from the group consisting of baby hamster kidney cells, mouse cells, human embryo cells, and chinese hamster ovary cells.

22. A host cell according to claim 19, wherein said host cell is an insect cell.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
( A ) LENGTH: 3635 base pairs
( B ) TYPE: nucleic acid (C) STRANDEDNESS: single
(D) TOPOLOGY: linear (ii) MOLECULE TYPE: cDNA (ix) FEATURE:
(A) NAME/KEY: CDS
(B) LOCATION: 138..3137

(xi) SEQUENCE DESCRIPTION: SEQ ID NO:1:

```
GAATTCGTGT CTCGGCACTC ACTCCCGGCC GCCCGGACAG GGAGCTTTCG CTGGCGCGCT        60

TGGCCGGCGA CAGGACAGGT TCGGGACGTC CATCTGTCCA TCCGTCCGGA GAGAAATTAC       120

AGATCCGCAG CCCCGGG ATG GGG CCG GCC CCG CTG CCG CTG CTG CTG GGC         170
                Met Gly Pro Ala Pro Leu Pro Leu Leu Leu Gly
                  1               5                      10

CTC TTC CTC CCC GCG CTC TGG CGT AGA GCT ATC ACT GAG GCA AGG GAA         218
Leu Phe Leu Pro Ala Leu Trp Arg Arg Ala Ile Thr Glu Ala Arg Glu
              15                  20                  25

GAA GCC AAG CCT TAC CCG CTA TTC CCG GGA CCT TTT CCA GGG AGC CTG         266
Glu Ala Lys Pro Tyr Pro Leu Phe Pro Gly Pro Phe Pro Gly Ser Leu
         30                  35                  40

CAA ACT GAC CAC ACA CCG CTG TTA TCC CTT CCT CAC GCC AGT GGG TAC         314
Gln Thr Asp His Thr Pro Leu Leu Ser Leu Pro His Ala Ser Gly Tyr
     45                  50                  55

CAG CCT GCC TTG ATG TTT TCA CCA ACC CAG CCT GGA AGA CCA CAT ACA         362
Gln Pro Ala Leu Met Phe Ser Pro Thr Gln Pro Gly Arg Pro His Thr
 60                  65                  70                  75

GGA AAC GTA GCC ATT CCC CAG GTG ACC TCT GTC GAA TCA AAG CCC CTA         410
Gly Asn Val Ala Ile Pro Gln Val Thr Ser Val Glu Ser Lys Pro Leu
                 80                  85                  90

CCG CCT CTT GCC TTC AAA CAC ACA GTT GGA CAC ATA ATA CTT TCT GAA         458
Pro Pro Leu Ala Phe Lys His Thr Val Gly His Ile Ile Leu Ser Glu
             95                 100                 105

CAT AAA GGT GTC AAA TTT AAT TGC TCA ATC AAT GTA CCT AAT ATA TAC         506
His Lys Gly Val Lys Phe Asn Cys Ser Ile Asn Val Pro Asn Ile Tyr
         110                 115                 120

CAG GAC ACC ACA ATT TCT TGG TGG AAA GAT GGG AAG GAA TTG CTT GGG         554
Gln Asp Thr Thr Ile Ser Trp Trp Lys Asp Gly Lys Glu Leu Leu Gly
     125                 130                 135

GGA CAT CAT CGA ATT ACA CAG TTT TAT CCA GAT GAT GAA GTT ACA GCA         602
Gly His His Arg Ile Thr Gln Phe Tyr Pro Asp Asp Glu Val Thr Ala
140                 145                 150                 155

ATA ATC GCT TCC TTC AGC ATA ACC AGT GTG CAG CGT TCA GAC AAT GGG         650
Ile Ile Ala Ser Phe Ser Ile Thr Ser Val Gln Arg Ser Asp Asn Gly
                 160                 165                 170

TCG TAT ATC TGT AAG ATG AAA ATA AAC AAT GAA GAG ATC GTG TCT GAT         698
Ser Tyr Ile Cys Lys Met Lys Ile Asn Asn Glu Glu Ile Val Ser Asp
             175                 180                 185

CCC ATC TAC ATC GAA GTA CAA GGA CTT CCT CAC TTT ACT AAG CAG CCT         746
Pro Ile Tyr Ile Glu Val Gln Gly Leu Pro His Phe Thr Lys Gln Pro
         190                 195                 200

GAG AGC ATG AAT GTC ACC AGA AAC ACA GCC TTC AAC CTC ACC TGT CAG         794
Glu Ser Met Asn Val Thr Arg Asn Thr Ala Phe Asn Leu Thr Cys Gln
 205                 210                 215

GCT GTG GGC CCG CCT GAG CCC GTC AAC ATT TTC TGG GTT CAA AAC AGT         842
Ala Val Gly Pro Pro Glu Pro Val Asn Ile Phe Trp Val Gln Asn Ser
220                 225                 230                 235

AGC CGT GTT AAC GAA CAG CCT GAA AAA TCC CCC GGC GTG CTA ACT GTT         890
Ser Arg Val Asn Glu Gln Pro Glu Lys Ser Pro Gly Val Leu Thr Val
                 240                 245                 250

CCA GGC CTG ACG GAG ATG GCG GTC TTC AGT TGT GAG GCC CAC AAT GAC         938
```

| | | | | | | | | | | | | | | | | |
|---|---|---|---|---|---|---|---|---|---|---|---|---|---|---|---|---|
| Pro | Gly | Leu | Thr 255 | Glu | Met | Ala | Val | Phe 260 | Ser | Cys | Glu | Ala | His 265 | Asn | Asp | |
| AAA Lys | GGG Gly | CTG Leu 270 | ACC Thr | GTG Val | TCC Ser | CAG Gln | GGA Gly 275 | GTG Val | CAG Gln | ATC Ile | AAC Asn | ATC Ile 280 | AAA Lys | GCA Ala | ATT Ile | 986 |
| CCC Pro | TCC Ser 285 | CCA Pro | CCA Pro | ACT Thr | GAA Glu | GTC Val 290 | AGC Ser | ATC Ile | CGT Arg | AAC Asn | AGC Ser 295 | ACT Thr | GCA Ala | CAC His | AGC Ser | 1034 |
| ATT Ile 300 | CTG Leu | ATC Ile | TCC Ser | TGG Trp | GTT Val 305 | CCT Pro | GGT Gly | TTT Phe | GAT Asp | GGA Gly 310 | TAC Tyr | TCC Ser | CCG Pro | TTC Phe | AGG Arg 315 | 1082 |
| AAT Asn | TGC Cys | AGC Ser | ATT Ile | CAG Gln 320 | GTC Val | AAG Lys | GAA Glu | GCT Ala | GAT Asp 325 | CCG Pro | CTG Leu | GGT Gly | AAT Asn | GGC Gly 330 | TCA Ser | 1130 |
| GTC Val | ATG Met | ATT Ile | TTT Phe 335 | AAC Asn | ACC Thr | TCT Ser | GCC Ala | TTA Leu 340 | CCA Pro | CAT His | CTG Leu | TAC Tyr | CAA Gln 345 | ATC Ile | AAG Lys | 1178 |
| CAG Gln | CTG Leu | CAA Gln 350 | GCC Ala | CTG Leu | GCT Ala | AAT Asn | TAC Tyr 355 | AGC Ser | ATT Ile | GGT Gly | GTT Val | TCC Ser 360 | TGC Cys | ATG Met | AAT Asn | 1226 |
| GAA Glu | ATA Ile 365 | GGC Gly | TGG Trp | TCT Ser | GCA Ala | GTG Val 370 | AGC Ser | CCT Pro | TGG Trp | ATT Ile | CTA Leu 375 | GCA Ala | AGC Ser | ACG Thr | ACT Thr | 1274 |
| GAA Glu 380 | GGA Gly | GCC Ala | CCA Pro | TCA Ser | GTA Val 385 | GCA Ala | CCT Pro | TTA Leu | AAT Asn | GTC Val 390 | ACT Thr | GTG Val | TTT Phe | CTG Leu | AAT Asn 395 | 1322 |
| GAA Glu | TCT Ser | AGT Ser | GAT Asp | AAT Asn 400 | GTG Val | GAC Asp | ATC Ile | AGA Arg | TGG Trp 405 | ATG Met | AAG Lys | CCT Pro | CCG Pro | ACT Thr 410 | AAG Lys | 1370 |
| CAG Gln | CAG Gln | GAT Asp | GGA Gly 415 | GAA Glu | CTG Leu | GTG Val | GGC Gly | TAC Tyr 420 | CGG Arg | ATA Ile | TCC Ser | CAC His | GTG Val 425 | TGG Trp | CAG Gln | 1418 |
| AGT Ser | GCA Ala | GGG Gly | ATT Ile 430 | TCC Ser | AAA Lys | GAG Glu | CTC Leu | TTG Leu 435 | GAG Glu | GAA Glu | GTT Val | GGC Gly | CAG Gln 440 | AAT Asn | GGC Gly | 1466 |
| AGC Ser | CGA Arg 445 | GCT Ala | CGG Arg | ATC Ile | TCT Ser | GTT Val 450 | CAA Gln | GTC Val | CAC His | AAT Asn | GCT Ala 455 | ACG Thr | TGC Cys | ACA Thr | GTG Val | 1514 |
| AGG Arg 460 | ATT Ile | GCA Ala | GCC Ala | GTC Val | ACC Thr 465 | AGA Arg | GGG Gly | GGA Gly | GTT Val | GGG Gly 470 | CCC Pro | TTC Phe | AGT Ser | GAT Asp | CCA Pro 475 | 1562 |
| GTG Val | AAA Lys | ATA Ile | TTT Phe | ATC Ile 480 | CCT Pro | GCA Ala | CAC His | GGT Gly | TGG Trp 485 | GTA Val | GAT Asp | TAT Tyr | GCC Ala | CCC Pro 490 | TCT Ser | 1610 |
| TCA Ser | ACT Thr | CCG Pro | GCG Ala 495 | CCT Pro | GGC Gly | AAC Asn | GCA Ala | GAT Asp 500 | CCT Pro | GTG Val | CTC Leu | ATC Ile | ATC Ile 505 | TTT Phe | GGC Gly | 1658 |
| TGC Cys | TTT Phe | TGT Cys 510 | GGA Gly | TTT Phe | ATT Ile | TTG Leu | ATT Ile 515 | GGG Gly | TTG Leu | ATT Ile | TTA Leu | TAC Tyr 520 | ATC Ile | TCC Ser | TTG Leu | 1706 |
| GCC Ala | ATC Ile 525 | AGA Arg | AAA Lys | AGA Arg | GTC Val | CAG Gln 530 | GAG Glu | ACA Thr | AAG Lys | TTT Phe | GGG Gly 535 | AAT Asn | GCA Ala | TTC Phe | ACA Thr | 1754 |
| GAG Glu | GAG Glu | GAT Asp | TCT Ser | GAA Glu 540 | TTA Leu | GTG Val | GTG Val | AAT Asn | TAT Tyr 545 | ATA Ile | GCA Ala | AAG Lys | AAA Lys | TCC Ser 550 | TTC Phe | 1802 |
| TGT Cys 555 | CGG Arg | CGA Arg | GCC Ala | ATT Ile | GAA Glu 560 | CTT Leu | ACC Thr | TTA Leu | CAT His | AGC Ser 565 | TTG Leu | GGA Gly | GTC Val | AGT Ser | GAG Glu 570 | 1850 |
| GAA Glu | CTA Leu | CAA Gln | AAT Asn | AAA Lys | CTA Leu | GAA Glu | GAT Asp | GTT Val | GTG Val | ATT Ile | GAC Asp | AGG Arg | AAT Asn | CTT Leu | CTA Leu | 1898 |

-continued

| | | | | | | | | | | | | | | | | |
|---|---|---|---|---|---|---|---|---|---|---|---|---|---|---|---|---|
| Glu | Leu | Gln | Asn 575 | Lys | Leu | Glu | Asp 580 | Val | Ile | Asp | Arg | Asn 585 | Leu | Leu | | |
| ATT | CTT | GGA | AAA | ATT | CTG | GGT | GAA | GGA | GAG | TTT | GGG | TCT | GTA | ATG | GAA | 1946 |
| Ile | Leu | Gly 590 | Lys | Ile | Leu | Gly | Glu 595 | Gly | Glu | Phe | Gly | Ser 600 | Val | Met | Glu | |
| GGA | AAT | CTT | AAG | CAG | GAA | GAT | GGG | ACC | TCT | CTG | AAA | GTG | GCA | GTG | AAG | 1994 |
| Gly | Asn | Leu 605 | Lys | Gln | Glu | Asp | Gly 610 | Thr | Ser | Leu | Lys | Val 615 | Ala | Val | Lys | |
| ACC | ATG | AAG | TTG | GAC | AAC | TCT | TCA | CAT | CGG | GAG | ATC | GAG | GAG | TTT | CTC | 2042 |
| Thr 620 | Met | Lys | Leu | Asp | Asn 625 | Ser | Ser | His | Arg | Glu 630 | Ile | Glu | Glu | Phe | Leu 635 | |
| AGT | GAG | GCA | GCG | TGC | ATG | AAA | GAC | TTC | AGC | CAC | CCA | AAT | GTC | ATT | CGA | 2090 |
| Ser | Glu | Ala | Ala | Cys 640 | Met | Lys | Asp | Phe | Ser 645 | His | Pro | Asn | Val | Ile 650 | Arg | |
| CTT | CTA | GGT | GTG | TGT | ATA | GAA | ATG | AGC | TCT | CAA | GGC | ATC | CCA | AAG | CCC | 2138 |
| Leu | Leu | Gly 655 | Val | Cys | Ile | Glu | Met 660 | Ser | Ser | Gln | Gly | Ile 665 | Pro | Lys | Pro | |
| ATG | GTA | ATT | TTA | CCC | TTC | ATG | AAA | TAC | GGG | GAC | CTG | CAT | ACT | TAC | TTA | 2186 |
| Met | Val | Ile 670 | Leu | Pro | Phe | Met | Lys 675 | Tyr | Gly | Asp | Leu | His 680 | Thr | Tyr | Leu | |
| CTT | TAT | TCC | CGA | TTG | GAG | ACA | GGA | CCA | AAG | CAT | ATT | CCT | CTG | CAG | ACA | 2234 |
| Leu | Tyr 685 | Ser | Arg | Leu | Glu | Thr 690 | Gly | Pro | Lys | His | Ile 695 | Pro | Leu | Gln | Thr | |
| CTA | TTG | AAG | TTC | ATG | GTG | GAT | ATT | GCC | CTG | GGA | ATG | GAG | TAT | CTG | AGC | 2282 |
| Leu 700 | Leu | Lys | Phe | Met | Val 705 | Asp | Ile | Ala | Leu | Gly 710 | Met | Glu | Tyr | Leu | Ser 715 | |
| AAC | AGG | AAT | TTT | CTT | CAT | CGA | GAT | TTA | GCT | GCT | CGA | AAC | TGC | ATG | TTG | 2330 |
| Asn | Arg | Asn | Phe | Leu 720 | His | Arg | Asp | Leu | Ala 725 | Ala | Arg | Asn | Cys | Met 730 | Leu | |
| CGA | GAT | GAC | ATG | ACT | GTC | TGT | GTT | GCG | GAC | TTC | GGC | CTC | TCT | AAG | AAG | 2378 |
| Arg | Asp | Asp | Met | Thr 735 | Val | Cys | Val | Ala | Asp 740 | Phe | Gly | Leu | Ser | Lys 745 | Lys | |
| ATT | TAC | AGT | GGC | GAT | TAT | TAC | CGC | CAA | GGC | CGC | ATT | GCT | AAG | ATG | CCT | 2426 |
| Ile | Tyr | Ser 750 | Gly | Asp | Tyr | Tyr | Arg 755 | Gln | Gly | Arg | Ile | Ala 760 | Lys | Met | Pro | |
| GTT | AAA | TGG | ATC | GCC | ATA | GAA | AGT | CTT | GCA | GAC | CGA | GTC | TAC | ACA | AGT | 2474 |
| Val | Lys 765 | Trp | Ile | Ala | Ile | Glu 770 | Ser | Leu | Ala | Asp | Arg 775 | Val | Tyr | Thr | Ser | |
| AAA | AGT | GAT | GTG | TGG | GCA | TTT | GGC | GTG | ACC | ATG | TGG | GAA | ATA | CGT | ACG | 2522 |
| Lys 780 | Ser | Asp | Val | Trp | Ala 785 | Phe | Gly | Val | Thr | Met 790 | Trp | Glu | Ile | Arg | Thr 795 | |
| CGG | GGA | ATG | ACT | CCC | TAT | CCT | GGG | GTC | CAG | AAC | CAT | GAG | ATG | TAT | GAC | 2570 |
| Arg | Gly | Met | Thr | Pro 800 | Tyr | Pro | Gly | Val | Gln 805 | Asn | His | Glu | Met | Tyr 810 | Asp | |
| TAT | CTT | CTC | CAT | GGC | CAC | AGG | TTG | AAG | CAG | CCC | GAA | GAC | TGC | CTG | GAT | 2618 |
| Tyr | Leu | Leu | His 815 | Gly | His | Arg | Leu | Lys 820 | Gln | Pro | Glu | Asp | Cys 825 | Leu | Asp | |
| GAA | CTG | TAT | GAA | ATA | ATG | TAC | TCT | TGC | TGG | AGA | ACC | GAT | CCC | TTA | GAC | 2666 |
| Glu | Leu | Tyr 830 | Glu | Ile | Met | Tyr | Ser 835 | Cys | Trp | Arg | Thr | Asp 840 | Pro | Leu | Asp | |
| CGC | CCC | ACC | TTT | TCA | GTA | TTG | AGG | CTG | CAG | CTA | GAA | AAA | CTC | TTA | GAA | 2714 |
| Arg | Pro | Thr 845 | Phe | Ser | Val | Leu | Arg 850 | Leu | Gln | Leu | Glu | Lys 855 | Leu | Leu | Glu | |
| AGT | TTG | CCT | GAC | GTT | CGG | AAC | CAA | GCA | GAC | GTT | ATT | TAC | GTC | AAT | ACA | 2762 |
| Ser 860 | Leu | Pro | Asp | Val | Arg 865 | Asn | Gln | Ala | Asp | Val 870 | Ile | Tyr | Val | Asn | Thr 875 | |
| CAG | TTG | CTG | GAG | AGC | TCT | GAG | GGC | CTG | GCC | CAG | GGC | CCC | ACC | CTT | GCT | 2810 |
| Gln | Leu | Leu | Glu | Ser 880 | Ser | Glu | Gly | Leu | Ala 885 | Gln | Gly | Pro | Thr | Leu 890 | Ala | |
| CCA | CTG | GAC | TTG | AAC | ATC | GAC | CCT | GAC | TCT | ATA | ATT | GCC | TCC | TGC | ACT | 2858 |

```
Pro  Leu  Asp  Leu  Asn  Ile  Asp  Pro  Asp  Ser  Ile  Ile  Ala  Ser  Cys  Thr
               895                 900                      905

CCC  CGC  GCT  GCC  ATC  AGT  GTG  GTC  ACA  GCA  GAA  GTT  CAT  GAC  AGC  AAA        2906
Pro  Arg  Ala  Ala  Ile  Ser  Val  Val  Thr  Ala  Glu  Val  His  Asp  Ser  Lys
          910                      915                      920

CCT  CAT  GAA  GGA  CGG  TAC  ATC  CTG  AAT  GGG  GGC  AGT  GAG  GAA  TGG  GAA        2954
Pro  His  Glu  Gly  Arg  Tyr  Ile  Leu  Asn  Gly  Gly  Ser  Glu  Glu  Trp  Glu
     925                      930                      935

GAT  CTG  ACT  TCT  GCC  CCC  TCT  GCT  GCA  GTC  ACA  GCT  GAA  AAG  AAC  AGT        3002
Asp  Leu  Thr  Ser  Ala  Pro  Ser  Ala  Ala  Val  Thr  Ala  Glu  Lys  Asn  Ser
940                      945                      950                      955

GTT  TTA  CCG  GGG  GAG  AGA  CTT  GTT  AGG  AAT  GGG  GTC  TCC  TGG  TCC  CAT        3050
Val  Leu  Pro  Gly  Glu  Arg  Leu  Val  Arg  Asn  Gly  Val  Ser  Trp  Ser  His
                    960                      965                      970

TCG  AGC  ATG  CTG  CCC  TTG  GGA  AGC  TCA  TTG  CCC  GAT  GAA  CTT  TTG  TTT        3098
Ser  Ser  Met  Leu  Pro  Leu  Gly  Ser  Ser  Leu  Pro  Asp  Glu  Leu  Leu  Phe
               975                      980                      985

GCT  GAC  GAC  TCC  TCA  GAA  GGC  TCA  GAA  GTC  CTG  ATG  TGA  GGAGAGGTGC            3147
Ala  Asp  Asp  Ser  Ser  Glu  Gly  Ser  Glu  Val  Leu  Met  *
          990                      995                1000

GGGGAGACAT TCCAAAAATC AAGCCAATTC TTCTGCTGTA GGAGAATCCA ATTGTACCTG                      3207

ATGTTTTTGG TATTTGTCTT CCTTACCAAG TGAACTCCAT GGCCCCAAAG CACCAGATGA                      3267

ATGTTGTTAA GGAAGCTGTC ATTAAAATA CATAATATAT ATTTATTTAA AGAGAAAAAA                       3327

TATGTGTATA TCATGAAAAA GACAAGGATA TTTTAATAAA ACATTACTTA TTTCATTTCA                      3387

CTTATCTTGC ATATCTTAAA ATTAAGCTTC AGCTGCTCCT TGATATTAAC CTTTGTACAG                      3447

AGTTGAAGTT GTTTTTCAA CTTCTTTTCT TTTTCATTAC TATTAAATGT AAAAATATTT                       3507

GTAAAATGAA ATGCCATATT TGACTTGGCT TCTGGTCTTG ATGTATTTGA TAAGAATGAT                      3567

TAATTTTCTG ATATGGCTTC CATAATAAAA TTGAAATAGG AAAAAAAAAA AAAAAAAAA                       3627

AAAAAAAA                                                                                3635
```

( 2 ) INFORMATION FOR SEQ ID NO:2:

( i ) SEQUENCE CHARACTERISTICS:
        ( A ) LENGTH: 999 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Gly  Pro  Ala  Pro  Leu  Pro  Leu  Leu  Leu  Gly  Leu  Phe  Leu  Pro  Ala
 1              5                   10                      15

Leu  Trp  Arg  Arg  Ala  Ile  Thr  Glu  Ala  Arg  Glu  Glu  Ala  Lys  Pro  Tyr
               20                  25                      30

Pro  Leu  Phe  Pro  Gly  Pro  Phe  Pro  Gly  Ser  Leu  Gln  Thr  Asp  His  Thr
          35                  40                      45

Pro  Leu  Leu  Ser  Leu  Pro  His  Ala  Ser  Gly  Tyr  Gln  Pro  Ala  Leu  Met
          50                  55                      60

Phe  Ser  Pro  Thr  Gln  Pro  Gly  Arg  Pro  His  Thr  Gly  Asn  Val  Ala  Ile
 65                  70                      75                           80

Pro  Gln  Val  Thr  Ser  Val  Glu  Ser  Lys  Pro  Leu  Pro  Leu  Ala  Phe
                    85                  90                      95

Lys  His  Thr  Val  Gly  His  Ile  Ile  Leu  Ser  Glu  His  Lys  Gly  Val  Lys
               100                     105                     110

Phe  Asn  Cys  Ser  Ile  Asn  Val  Pro  Asn  Ile  Tyr  Gln  Asp  Thr  Thr  Ile
          115                     120                     125
```

```
Ser  Trp  Trp  Lys  Asp  Gly  Lys  Glu  Leu  Leu  Gly  Gly  His  His  Arg  Ile
     130                 135                      140
Thr  Gln  Phe  Tyr  Pro  Asp  Asp  Glu  Val  Thr  Ala  Ile  Ile  Ala  Ser  Phe
145                      150                 155                           160
Ser  Ile  Thr  Ser  Val  Gln  Arg  Ser  Asp  Asn  Gly  Ser  Tyr  Ile  Cys  Lys
               165                      170                      175
Met  Lys  Ile  Asn  Asn  Glu  Glu  Ile  Val  Ser  Asp  Pro  Ile  Tyr  Ile  Glu
                180                 185                           190
Val  Gln  Gly  Leu  Pro  His  Phe  Thr  Lys  Gln  Pro  Glu  Ser  Met  Asn  Val
          195                      200                 205
Thr  Arg  Asn  Thr  Ala  Phe  Asn  Leu  Thr  Cys  Gln  Ala  Val  Gly  Pro  Pro
     210                      215                      220
Glu  Pro  Val  Asn  Ile  Phe  Trp  Val  Gln  Asn  Ser  Ser  Arg  Val  Asn  Glu
225                      230                 235                           240
Gln  Pro  Glu  Lys  Ser  Pro  Gly  Val  Leu  Thr  Val  Pro  Gly  Leu  Thr  Glu
               245                      250                      255
Met  Ala  Val  Phe  Ser  Cys  Glu  Ala  His  Asn  Asp  Lys  Gly  Leu  Thr  Val
                260                 265                           270
Ser  Gln  Gly  Val  Gln  Ile  Asn  Ile  Lys  Ala  Ile  Pro  Ser  Pro  Pro  Thr
          275                      280                 285
Glu  Val  Ser  Ile  Arg  Asn  Ser  Thr  Ala  His  Ser  Ile  Leu  Ile  Ser  Trp
     290                      295                      300
Val  Pro  Gly  Phe  Asp  Gly  Tyr  Ser  Pro  Phe  Arg  Asn  Cys  Ser  Ile  Gln
305                      310                 315                           320
Val  Lys  Glu  Ala  Asp  Pro  Leu  Gly  Asn  Gly  Ser  Val  Met  Ile  Phe  Asn
               325                      330                      335
Thr  Ser  Ala  Leu  Pro  His  Leu  Tyr  Gln  Ile  Lys  Gln  Leu  Gln  Ala  Leu
                340                 345                           350
Ala  Asn  Tyr  Ser  Ile  Gly  Val  Ser  Cys  Met  Asn  Glu  Ile  Gly  Trp  Ser
          355                      360                 365
Ala  Val  Ser  Pro  Trp  Ile  Leu  Ala  Ser  Thr  Thr  Glu  Gly  Ala  Pro  Ser
     370                      375                      380
Val  Ala  Pro  Leu  Asn  Val  Thr  Val  Phe  Leu  Asn  Glu  Ser  Ser  Asp  Asn
385                      390                 395                           400
Val  Asp  Ile  Arg  Trp  Met  Lys  Pro  Pro  Thr  Lys  Gln  Gln  Asp  Gly  Glu
               405                      410                      415
Leu  Val  Gly  Tyr  Arg  Ile  Ser  His  Val  Trp  Gln  Ser  Ala  Gly  Ile  Ser
                420                 425                           430
Lys  Glu  Leu  Leu  Glu  Glu  Val  Gly  Gln  Asn  Gly  Ser  Arg  Ala  Arg  Ile
          435                      440                 445
Ser  Val  Gln  Val  His  Asn  Ala  Thr  Cys  Thr  Val  Arg  Ile  Ala  Ala  Val
     450                      455                      460
Thr  Arg  Gly  Gly  Val  Gly  Pro  Phe  Ser  Asp  Pro  Val  Lys  Ile  Phe  Ile
465                      470                 475                           480
Pro  Ala  His  Gly  Trp  Val  Asp  Tyr  Ala  Pro  Ser  Ser  Thr  Pro  Ala  Pro
               485                      490                      495
Gly  Asn  Ala  Asp  Pro  Val  Leu  Ile  Ile  Phe  Gly  Cys  Phe  Cys  Gly  Phe
                500                 505                           510
Ile  Leu  Ile  Gly  Leu  Ile  Leu  Tyr  Ile  Ser  Leu  Ala  Ile  Arg  Lys  Arg
          515                      520                 525
Val  Gln  Glu  Thr  Lys  Phe  Gly  Asn  Ala  Phe  Thr  Glu  Glu  Asp  Ser  Glu
     530                      535                      540
Leu  Val  Val  Asn  Tyr  Ile  Ala  Lys  Lys  Ser  Phe  Cys  Arg  Arg  Ala  Ile
```

-continued

| 545 | | | | | 550 | | | | | 555 | | | | | 560 |
|---|---|---|---|---|---|---|---|---|---|---|---|---|---|---|---|
| Glu | Leu | Thr | Leu | His | Ser | Leu | Gly | Val | Ser | Glu | Glu | Leu | Gln | Asn | Lys |
| | | | | 565 | | | | | 570 | | | | | 575 | |
| Leu | Glu | Asp | Val | Val | Ile | Asp | Arg | Asn | Leu | Leu | Ile | Leu | Gly | Lys | Ile |
| | | | 580 | | | | | 585 | | | | | 590 | | |
| Leu | Gly | Glu | Gly | Glu | Phe | Gly | Ser | Val | Met | Glu | Gly | Asn | Leu | Lys | Gln |
| | | 595 | | | | | 600 | | | | | 605 | | | |
| Glu | Asp | Gly | Thr | Ser | Leu | Lys | Val | Ala | Val | Lys | Thr | Met | Lys | Leu | Asp |
| | 610 | | | | | 615 | | | | | 620 | | | | |
| Asn | Ser | Ser | His | Arg | Glu | Ile | Glu | Glu | Phe | Leu | Ser | Glu | Ala | Ala | Cys |
| 625 | | | | | 630 | | | | | 635 | | | | | 640 |
| Met | Lys | Asp | Phe | Ser | His | Pro | Asn | Val | Ile | Arg | Leu | Leu | Gly | Val | Cys |
| | | | | 645 | | | | | 650 | | | | | 655 | |
| Ile | Glu | Met | Ser | Ser | Gln | Gly | Ile | Pro | Lys | Pro | Met | Val | Ile | Leu | Pro |
| | | | 660 | | | | | 665 | | | | | 670 | | |
| Phe | Met | Lys | Tyr | Gly | Asp | Leu | His | Thr | Tyr | Leu | Leu | Tyr | Ser | Arg | Leu |
| | | 675 | | | | | 680 | | | | | 685 | | | |
| Glu | Thr | Gly | Pro | Lys | His | Ile | Pro | Leu | Gln | Thr | Leu | Leu | Lys | Phe | Met |
| | 690 | | | | | 695 | | | | | 700 | | | | |
| Val | Asp | Ile | Ala | Leu | Gly | Met | Glu | Tyr | Leu | Ser | Asn | Arg | Asn | Phe | Leu |
| 705 | | | | | 710 | | | | | 715 | | | | | 720 |
| His | Arg | Asp | Leu | Ala | Ala | Arg | Asn | Cys | Met | Leu | Arg | Asp | Asp | Met | Thr |
| | | | | 725 | | | | | 730 | | | | | 735 | |
| Val | Cys | Val | Ala | Asp | Phe | Gly | Leu | Ser | Lys | Lys | Ile | Tyr | Ser | Gly | Asp |
| | | | 740 | | | | | 745 | | | | | 750 | | |
| Tyr | Tyr | Arg | Gln | Gly | Arg | Ile | Ala | Lys | Met | Pro | Val | Lys | Trp | Ile | Ala |
| | | 755 | | | | | 760 | | | | | 765 | | | |
| Ile | Glu | Ser | Leu | Ala | Asp | Arg | Val | Tyr | Thr | Ser | Lys | Ser | Asp | Val | Trp |
| | 770 | | | | | 775 | | | | | 780 | | | | |
| Ala | Phe | Gly | Val | Thr | Met | Trp | Glu | Ile | Arg | Thr | Arg | Gly | Met | Thr | Pro |
| 785 | | | | | 790 | | | | | 795 | | | | | 800 |
| Tyr | Pro | Gly | Val | Gln | Asn | His | Glu | Met | Tyr | Asp | Tyr | Leu | Leu | His | Gly |
| | | | | 805 | | | | | 810 | | | | | 815 | |
| His | Arg | Leu | Lys | Gln | Pro | Glu | Asp | Cys | Leu | Asp | Glu | Leu | Tyr | Glu | Ile |
| | | | 820 | | | | | 825 | | | | | 830 | | |
| Met | Tyr | Ser | Cys | Trp | Arg | Thr | Asp | Pro | Leu | Asp | Arg | Pro | Thr | Phe | Ser |
| | | 835 | | | | | 840 | | | | | 845 | | | |
| Val | Leu | Arg | Leu | Gln | Leu | Glu | Lys | Leu | Leu | Glu | Ser | Leu | Pro | Asp | Val |
| | 850 | | | | | 855 | | | | | 860 | | | | |
| Arg | Asn | Gln | Ala | Asp | Val | Ile | Tyr | Val | Asn | Thr | Gln | Leu | Leu | Glu | Ser |
| 865 | | | | | 870 | | | | | 875 | | | | | 880 |
| Ser | Glu | Gly | Leu | Ala | Gln | Gly | Pro | Thr | Leu | Ala | Pro | Leu | Asp | Leu | Asn |
| | | | | 885 | | | | | 890 | | | | | 895 | |
| Ile | Asp | Pro | Asp | Ser | Ile | Ile | Ala | Ser | Cys | Thr | Pro | Arg | Ala | Ala | Ile |
| | | | 900 | | | | | 905 | | | | | 910 | | |
| Ser | Val | Val | Thr | Ala | Glu | Val | His | Asp | Ser | Lys | Pro | His | Glu | Gly | Arg |
| | | | 915 | | | | | 920 | | | | | 925 | | |
| Tyr | Ile | Leu | Asn | Gly | Gly | Ser | Glu | Glu | Trp | Glu | Asp | Leu | Thr | Ser | Ala |
| | 930 | | | | | 935 | | | | | 940 | | | | |
| Pro | Ser | Ala | Ala | Val | Thr | Ala | Glu | Lys | Asn | Ser | Val | Leu | Pro | Gly | Glu |
| 945 | | | | | 950 | | | | | 955 | | | | | 960 |
| Arg | Leu | Val | Arg | Asn | Gly | Val | Ser | Trp | Ser | His | Ser | Ser | Met | Leu | Pro |
| | | | | 965 | | | | | 970 | | | | | 975 | |

| Leu | Gly | Ser | Ser<br>980 | Leu | Pro | Asp | Glu | Leu<br>985 | Leu | Phe | Ala | Asp | Asp<br>990 | Ser | Ser |
|---|---|---|---|---|---|---|---|---|---|---|---|---|---|---|---|
| Glu | Gly | Ser<br>995 | Glu | Val | Leu | Met | | 1000 | | | | | | | |

( 2 ) INFORMATION FOR SEQ ID NO:3:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

CCTTCCTGGG CATGGAGTCC T        21

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

GGAGCAATGA TCTTGATCTT C        21

( 2 ) INFORMATION FOR SEQ ID NO:5:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

CACCTCTGCC TTACCACATC T        21

( 2 ) INFORMATION FOR SEQ ID NO:6:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

ATCCACAAAA GCAGCCAAAG A        21

( 2 ) INFORMATION FOR SEQ ID NO:7:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

AAGTCAGCAT CCGTAACAGC A        21

( 2 ) INFORMATION FOR SEQ ID NO:8:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:8:

GCAAAGAGGA GTCAACAGTA G    21

( 2 ) INFORMATION FOR SEQ ID NO:9:

( i ) SEQUENCE CHARACTERISTICS:
    ( A ) LENGTH: 52 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:9:

CTTTCAAATA TGTGTTGAAA TCTCTCTTCT ACTGTTGACT CCTCTTTGCC TT    52